United States Patent [19]

Hatakoshi

[11] Patent Number: Plant 7,106

[45] Date of Patent: Jan. 16, 1990

[54] APPLE TREE

[75] Inventor: Kunio Hatakoshi, Matsumoto, Japan

[73] Assignee: Komachien Co., Ltd., Nagano, Japan

[21] Appl. No.: 170,966

[22] Filed: Mar. 18, 1988

[30] Foreign Application Priority Data

Jun. 22, 1987 [JP] Japan ..... 2356

[51] Int. Cl.[4] ..... A01H 5/00

[52] U.S. Cl. ..... Plt./34

[58] Field of Search ..... Plt. 34

*Primary Examiner*—Robert E. Bagwill

*Attorney, Agent, or Firm*—Armstrong, Nikaido, Marmelstein, Kubovcik & Murray

[57] ABSTRACT

Disclosed is an apple tree having a moderate vigor and a good spur-bearing habit and producing a medium size fruit maturing early in the season and earlier than 'Tsugaru'. The fruit has an oval shape and a conspicuous appearance caused by a relief of dense and large dots against a solid deep red colored surface, which overlays a yellowish green ground color skin, when not bagged. The flesh of the fruit is yellowish white, moderately juicy, crisp, and hard, and has a moderate sweetness, a relatively strong acidity, and an aromatic flavor, which give a good sweet-acid balance and an excellent dessert quality. The keeping quality of the fruit is superior as a cultivar maturing earlier than 'Tsugaru'.

12 Drawing Sheets

BACKGROUND OF THE VARIETY

The present invention relates to a new and distinct variety of apple tree obtained from a natural crossing of 'Tsugaru'. The fruit matures early in the season and earlier than 'Tsugaru'. The appearance of the fruit is conspicuous because of a relief of dense and large dots formed on a solid deep red skin. The flesh of the fruit has a good sweet-acid balance, an excellent dessert quality, and a superior keeping quality.

This breeding was aimed at obtaining a new variety of apple tree which can produce an early-maturing fruit having an excellent dessert quality. For this purpose, the seeds, which were obtained from a natural crossing of 'Tsugaru' at the Hatakoshi farm residing at 393 Niimura, Matsumoto-shi, Nagano-ken, Japan, were sown in the same farm in 1976. These seedlings were raised naturally without grafting and the like. Among the trees raised from these seedlings and having a first crop in 1984, only one tree, considered to be especially promising, was selected.

The thus-selected apple tree according to this invention was asexually reproduced by top-working onto a seven-year-old 'Fuji (Chōfu 2)' tree grown on M26 rootstock at the farm residing at 6716-3 Katagiri, Nakagawa-mura, Kamiina-gun, Nagano-ken in the spring of 1985. The fruit obtained from this top-worked tree was compared with the fruit of the most similar varieties 'Tsugaru' and 'Nebuta', and as a result, it was concluded that the fruit of this apple tree is clearly distinguishable from those of similar varieties. This new variety of apple tree according to this invention was named 'Benihazuki'. Of these similar varieties used for comparison, 'Tsugaru' is a female parent, and 'Nebuta' is a cultivar producing a solid scarlet-coloured skin fruit which has a high sweetness (about 15 in refractometer index) and relatively strong acidity, and matures earlier than 'Tsugaru', e.g., in early-to-mid August, in an area about 650 meters above sea level in Nagano-ken, Japan.

'Tsugaru', the female parent of 'Benihazuki', was selected from the seedlings of 'Golden Delicious'×'unknown' crossed by the Aomori prefectural apple experimental station in 1930, and is known as a main early-maturing cultivar in Japan. The main botanical characteristics of 'Tsugaru' are as follows.

Tree:

*Shape.*—Apt to be upright while young, then gradually spreading.

*Vigor.*—Medium.

*Bearing shoot.*—Few spurs (short), but many long.

*Predominance of axially flower bud.*—Medium.

*Thickness of one-year-old shoot.*—Thin.

*Length of internode.*—Long.

Leaves:

*Shape.*—Elongated.

*Length.*—Short.

*Length of petiole.*—Short.

Flowers:

*Size.*—Small.

*Color.*—Pale pink at full bloom, and deep pink at the unopened stage.

*Flowering time.*—Blooming in the middle of the season, the same as 'Golden Delicious', and, for example, in late-April, in an area about 650 meters above sea level in Nagano-ken, Japan.

*Physiological fruit drop.*—Above average pre-harvest droppings.

Fruit:

*Size.*—Medium, average weight 250–300 g.

*Shape.*—Oval.

*Basin.*—Medium width and depth.

*Cavity.*—Medium width and depth.

*Color of skin.*—Yellowish green ground color and a pale red colouring with red stripes. Colouring clear when using a bag, but dull toned if not bagged.

*Skin.*—Thin, smooth, little shininess, and abundant russet. Dots are small and few, thus inconspicuous.

*Colour of flesh.*—Yellow.

*Flesh.*—Fine, juicy, relatively hard (14.8 lbs.), almost no water core, and little browning.

*Taste.*—Moderate sweetness (12.4 in refractometer index), weak acidity (0.32% maleic acid content), and an excellent dessert quality. Aromatic flavor is weak.

*Maturity.*—Maturing early in the season, for example, in early-September, in an area about 650 meters above sea level in Nagano-ken, Japan.

*Keeping quality.*—Can be kept for two to three weeks on the shelf and for a relatively long time in cold storage. The quality is good for an early-maturing cultivar.

Resistance to pests and diseases: Strongly resistant to rough bark disorder, and almost no occurrence of Heart rot (Core rot).

SUMMARY OF THE VARIETY

The new variety of apple tree according to this invention has a moderate vigor and a good spur-bearing habit, and produces a fruit maturing early in the season and earlier than 'Tsugaru'. The fruit has an oval shape, a medium size, and a conspicuous appearance caused by a relief of dense and large dots against a solid deep red coloured surface, which overlays a yellowish green ground colour skin, when not bagged. The flesh of the fruit is yellowish white, moderately juicy, crisp, and hard, and has a moderate sweetness, a relatively strong acidity, and an aromatic flavor, which give a good sweet-acid balance and an excellent dessert quality. The keeping quality of the fruit is superior for an early-maturing cultivar earlier than 'Tsugaru'.

DESCRIPTION OF THE VARIETY

Figure 1:
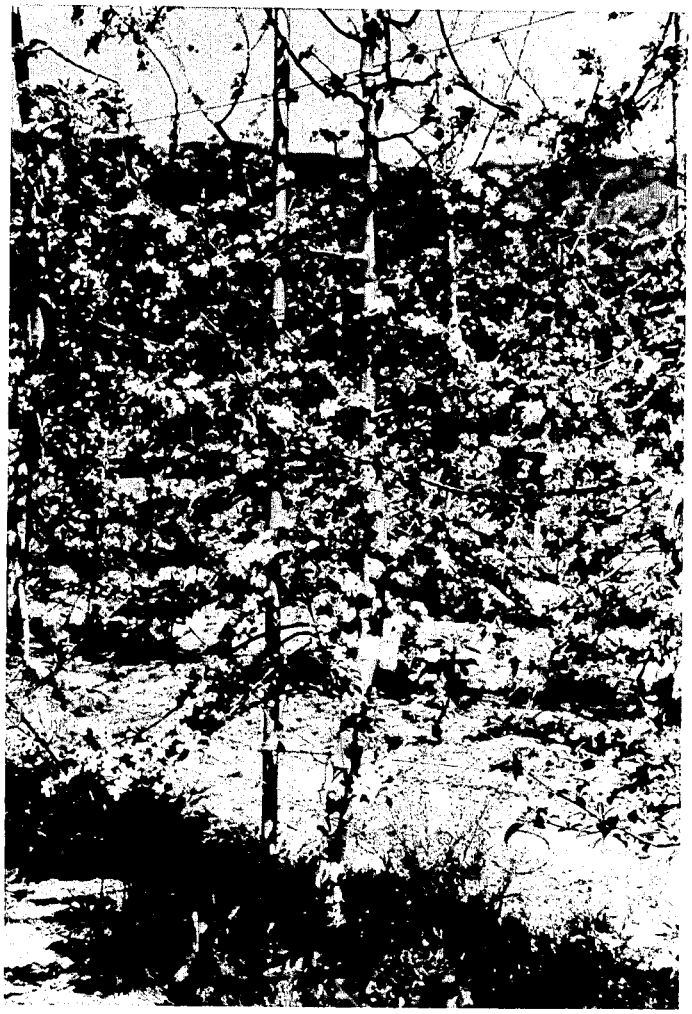
FIG. 1 is a photograph of a shape of the new and distinct variety of apple tree 'Benihazuki'.
Figure 2:
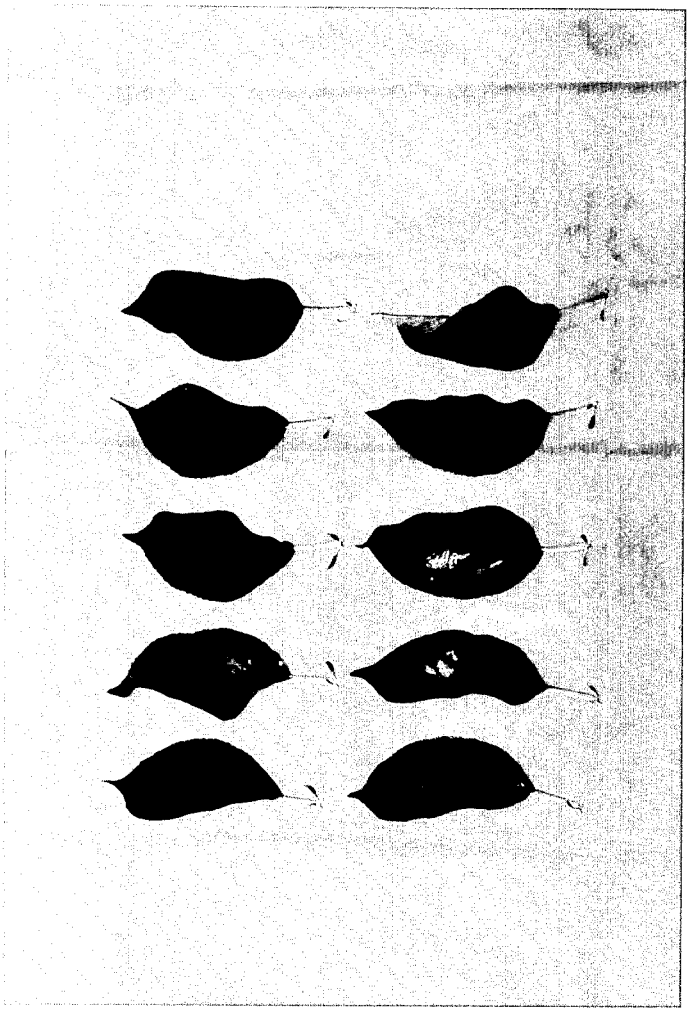
FIG. 2 is a photograph of adult leaves (upper side) of the new variety of apple tree.
Figure 3:
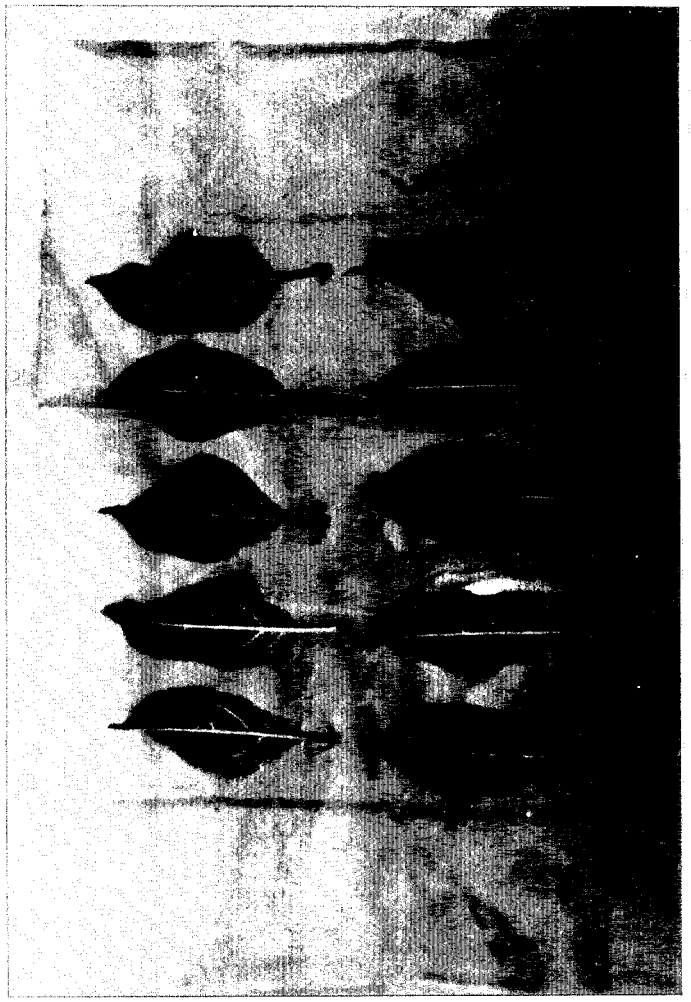
FIG. 3 is a photograph of adult leaves (reverse side) of the new variety of apple tree.
Figure 4:
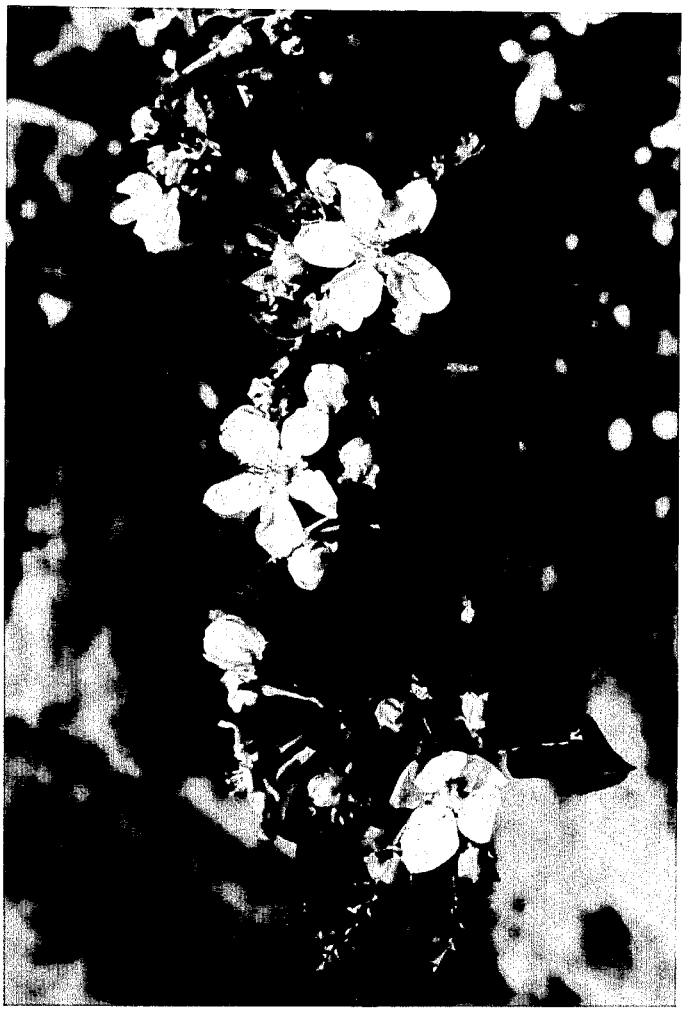
FIG. 4 is a photograph of the new variety of apple tree in blooming condition.
Figure 5:
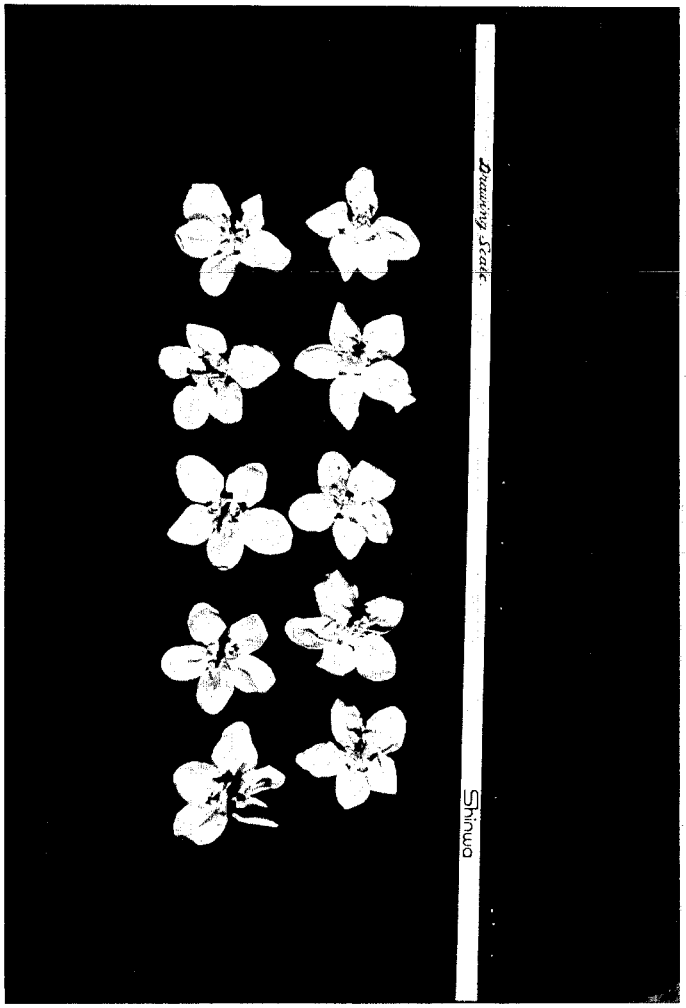
FIG. 5 is a photograph of flowers of the new variety of apple tree.
Figure 6:
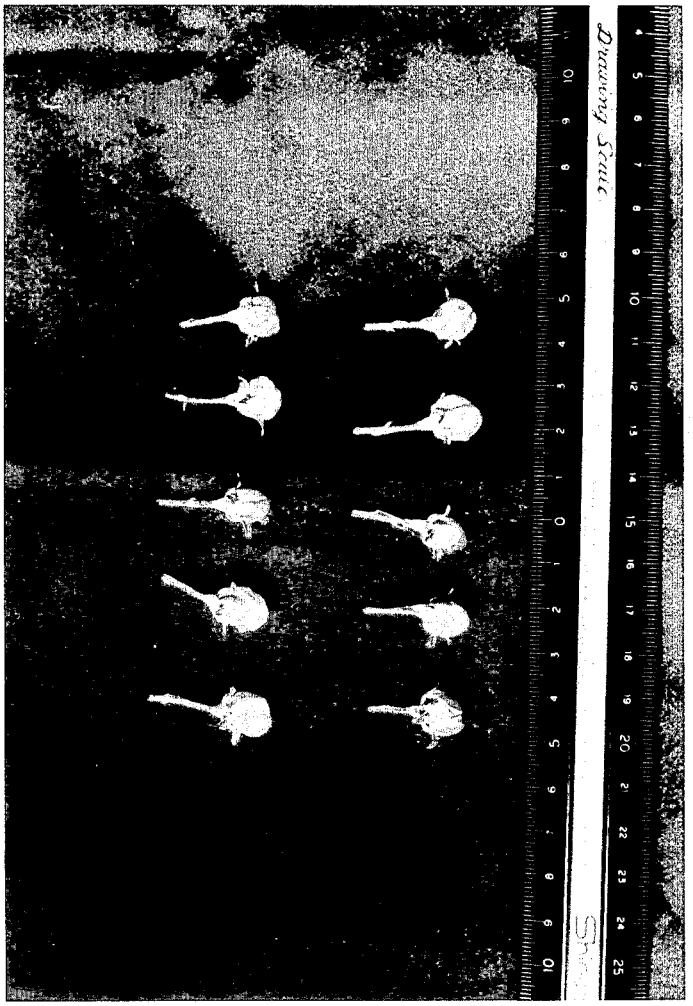
FIG. 6 is a photograph of flower buds of the new variety of apple tree.
Figure 7:
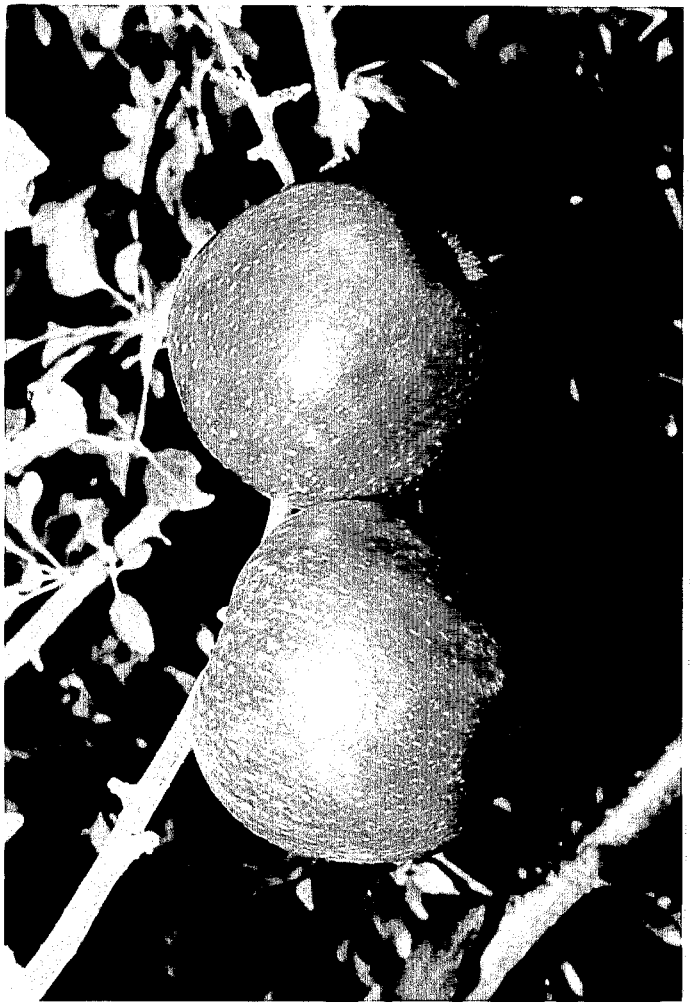
FIG. 7 is a photograph of the new variety of apple tree in bearing condition.
Figure 8:
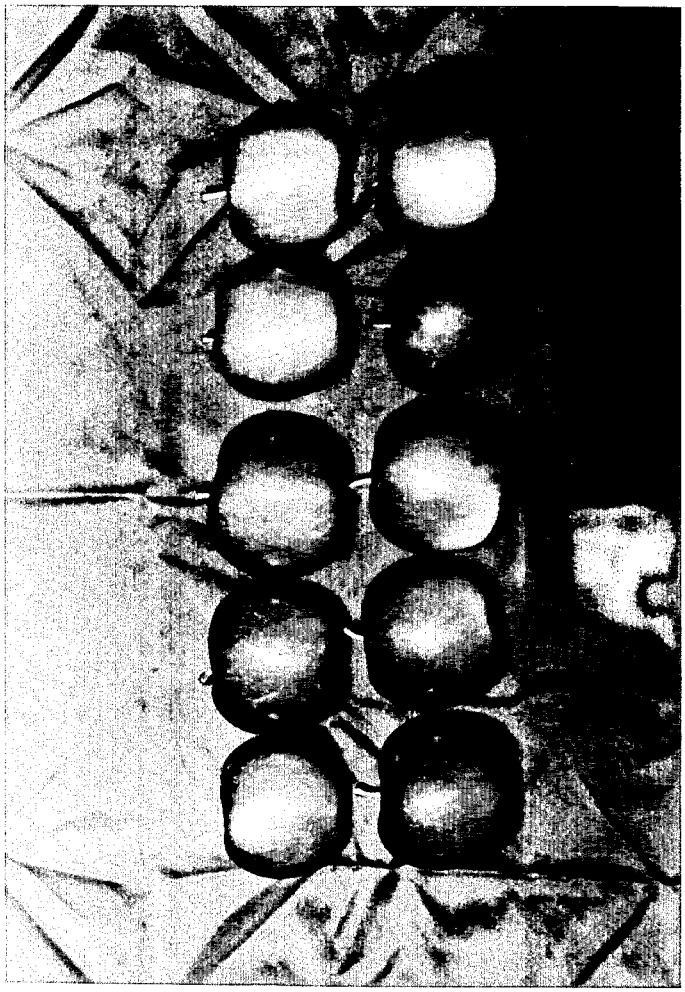
FIG. 8 is a photograph of side views of fruit of the new variety of apple tree.
Figure 9:
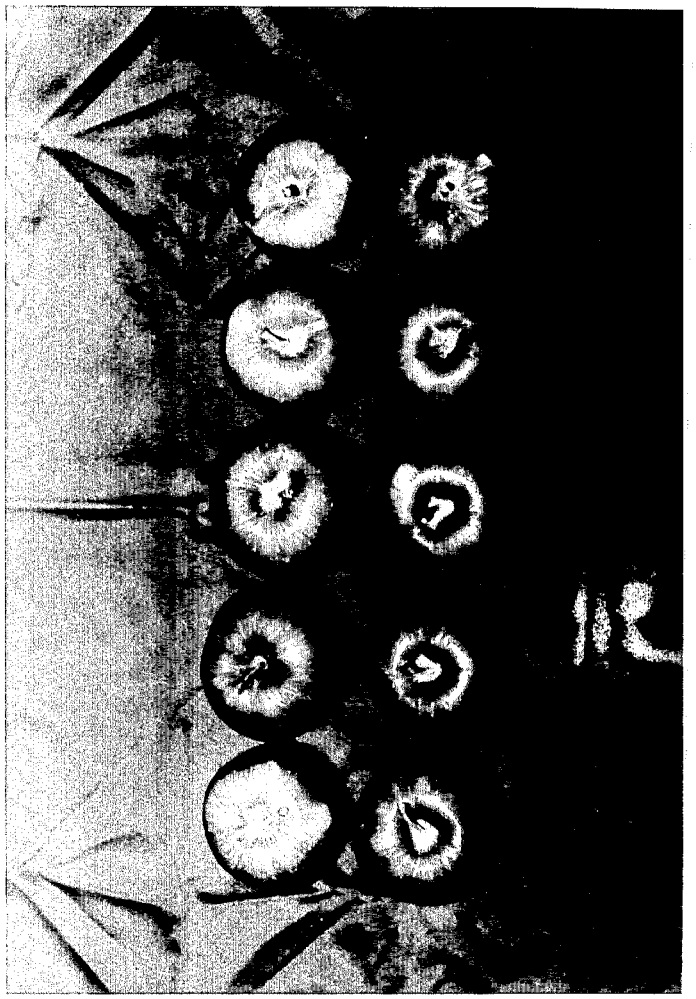
FIG. 9 is a photograph of cavities of fruit of the new variety of apple tree.
Figure 10:
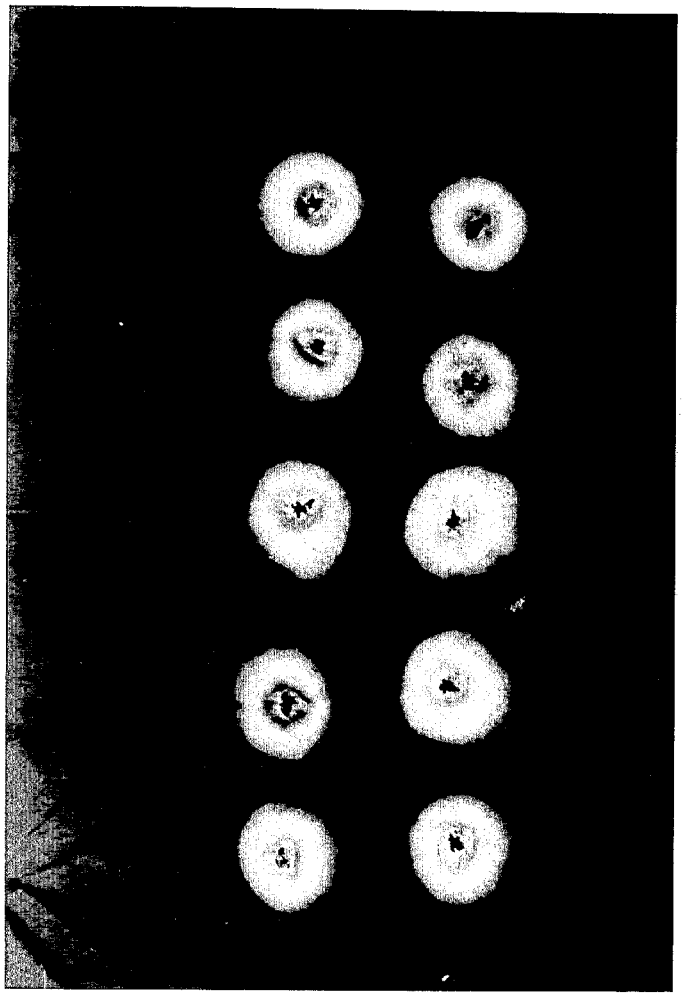
FIG. 10 is a photograph of basins of fruit of the new variety of apple tree.
Figure 11:
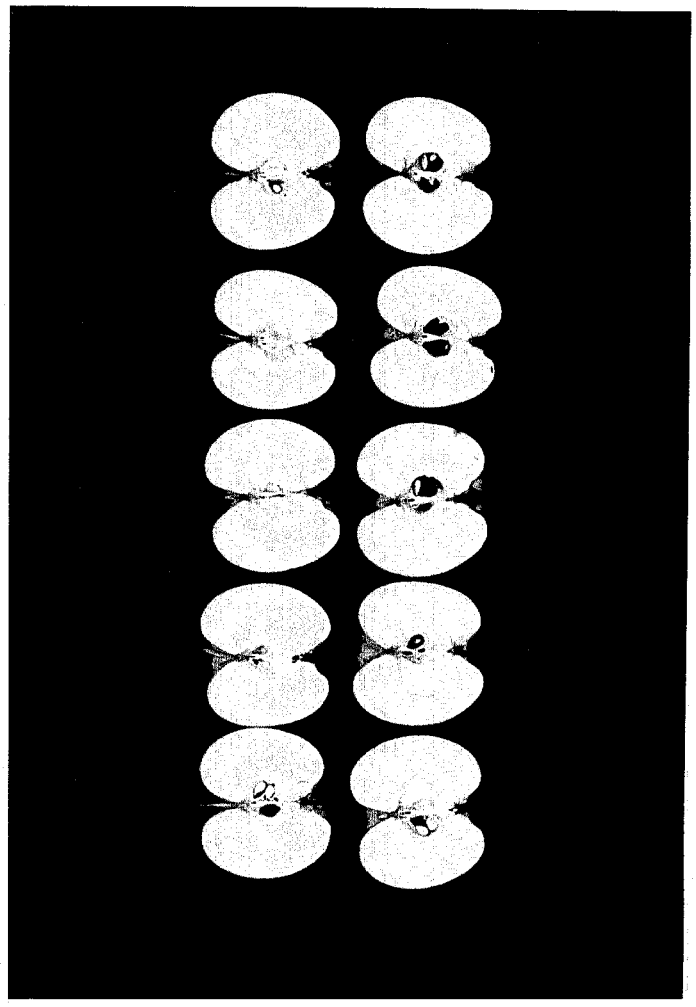
FIG. 11 is a photograph of longitudinal-sectional views of fruit of the new variety of apple tree; and, FIG. 12 is a photograph of cross-sectional views of fruit of the new variety of apple tree.
Figure 12:
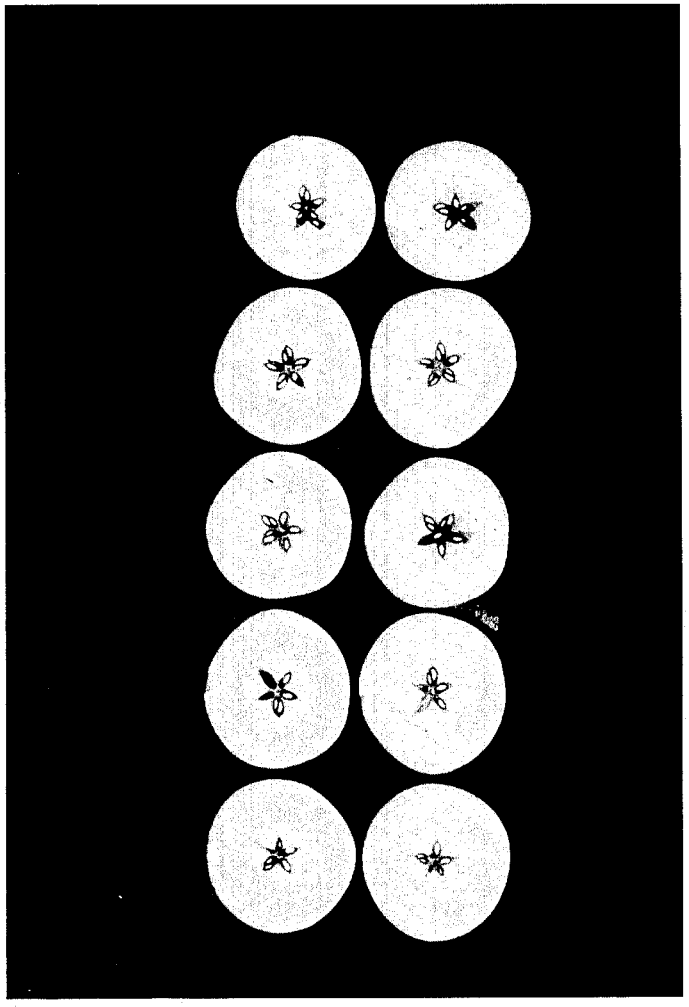

The botanical characteristics of the new and distinct variety of apple tree 'Benihazuki' are as follows.

Tree:

*Shape.*—Intermediate between upright and spreading.

*Vigor.*—Moderate.

*Spur.*—Bearing well.

*Auxiliary flower bud.*—Many.

*Thickness of one-year-old shoot.*—Thin.

*Length of internode.*—Short (2–2.5 cm).

Leaves:

*Shape.*—Elongated.

*Length.*—Short (about 8.7 cm).

*Colour.*—Green.

*Petiole.*—Long and of medium thickness.

Flowers:

*Size.*—Medium.

*Colour.*—White at full bloom, and deep pink at the unopened stage.

*Amount of pollen.*—Medium.

*Flowering time.*—Blooming at same time as 'Tsugaru', a few days earlier than 'Fuji', and, for example, in late-April, in an area about 650 meters above sea level in Nagano-ken, Japan.

*Physiological fruit drop.*—Slight or no early drop, and preharvest drop below average.

Fruit:

*Size.*—Medium, average weight about 250 g.

*Shape.*—Oval.

*Basin.*—Medium width and depth.

*Cavity.*—Medium width and depth.

*Color of skin.*—Yellowish green ground colour (corresponding to No. 3503 of the color chart of the Japan Color Standard for Horticultural Plants, hereinafter referred to as the JHS Color Chart) with a clear solid deep red colouring (corresponding to No. 0408 of the JHS Color Chart) when not bagged. No distinguishing stripe.

*Skin.*—Smooth surface, no russet, strong shininess. Showing a conspicuous appearance caused by a relief of dense and large dots against the aforementioned solid deep red coloured skin. Therefore, the appearance is quite different from that of 'Tsugaru'.

*Color of flesh.*—Yellowish white (corresponding to No. 2502 of the JHS Color Chart).

*Flesh.*—Moderately juicy, crisp, medium texture, hard (16 lbs.), and moderate browning. Water core occurring when fully ripe.

*Taste.*—Moderate sweetness (13–15 in refractometer index, which is a little higher than that of 'Tsugaru'), relatively strong acidity (about 0.56% maleic acid content, which is higher than 'Tsugaru' but falls rapidly after harvesting), no astringency, and an aromatic flavor, which give a good sweet-acid balance and an excellent dessert quality.

*Maturity.*—Maturing early in the season, 5–7 days earlier than 'Tsugaru', and, for example, in late-August, in an area about 650 meters above sea level in Nagano-ken, Japan.

*Keeping quality.*—Can be kept for about 30 days on the shelf and about 90 days in cold storage, for the fruit produced by the original tree raised from seedling. This quality is superior as a cultivar maturing earlier than 'Tsugaru'.

Resistance to pests and diseases: Almost no occurrence of Heart rot (Core rot). Moderately resistant to Alternaria blotch, Powdery mildew, rough bark disorder, and aphid, respectively.

The original tree of this new variety 'Benihazuki' is presently planted and maintained at the Hatakoshi farm residing at 393 Niimura, Matsumoto-shi, Nagano-ken, Japan.

I claim:

1. A new and distinct variety of apple tree, substantially as illustrated and described herein, characterized over known apple trees by (A) having a moderate vigor and a good spur-bearing habit, and (B) producing a medium size fruit having an oval shape (a) maturing early in the season and earlier than 'Tsugaru', and (b) having (1) a superior keeping quality for a cultivar maturing earlier than 'Tsugaru', (2) a conspicuous appearance caused by a relief of dense and large dots against a solid deep red coloured surface, which overlays a yellowish green ground colour skin, if not bagged, and (3) a yellowish white flesh which is moderately juicy, crisp and hard, has a moderate sweetness, a relatively strong acidity, and an aromatic flavor, and gives a good sweet-acid balance and an excellent dessert quality.

* * * * *

Drawing Scale
Shinua